Dec. 24, 1963 D. L. ARMSTRONG ETAL Plant Pat. 2,332
ROSE PLANT
Filed Dec. 18, 1962
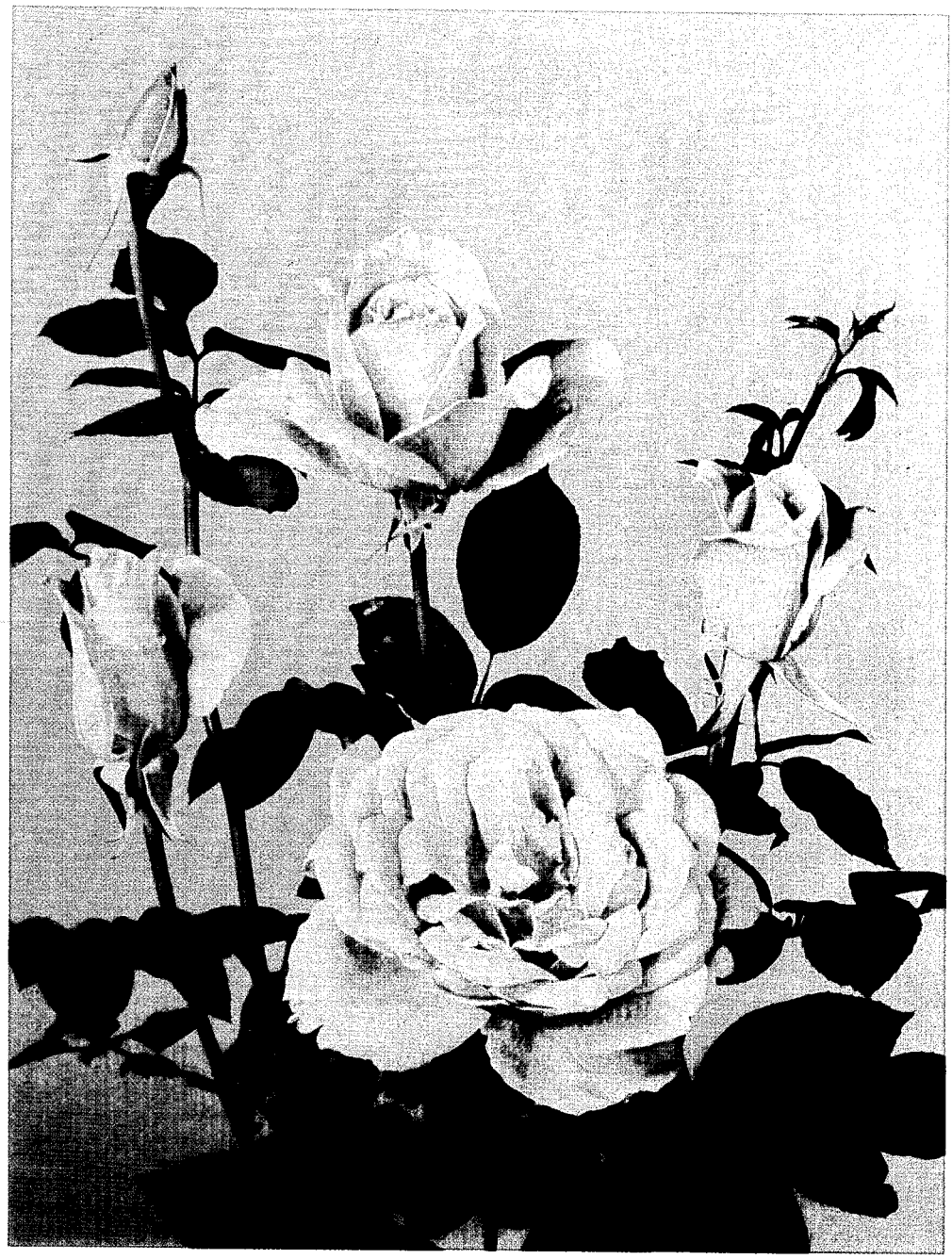
Inventors.
D. L. Armstrong
H. C. Swim
By: Robb & Robb
Attorneys.

United States Patent Office

Plant Pat. 2,332
Patented Dec. 24, 1963

2,332
ROSE PLANT

David L. Armstrong and Herbert C. Swim, Ontario, Calif., assignors to Armstrong Nurseries, Inc., Ontario, Calif., a corporation of California Filed Dec. 18, 1962, Ser. No. 245,630
1 Claim. (Cl. Plt.—18)

The present invention relates to a new and distinct variety of rose plant of the hybrid tea class, which was originated by us by crossing the variety "First Love" (Plant Patent No. 921) with an unnamed seedling which is the subject of Plant Patent No. 1,254, the former being the seed parent, and the latter being the pollen parent.

The general objective of this breeding was to produce an improved rose variety of the hybrid tea type, and in which the flower color falls in the range of pink, yellow, or pink-yellow blend, combined with quite double petalage, an attractive open flower form and strong fragrance, as well as a vigorous and attractive plant habit, with glossy foliage, and the flower buds of which have the exceptionally fine urn-shaped form of the seed parent, "First Love." These objectives were substantially achieved, along with other desirable improvements, as evidenced by the following characteristics which are outstanding in our new variety and which distinguish it from its parents, as well as from all other varieties of which we are aware.

(1) Relatively upright and exceptionally vigorous plant habits;

(2) A habit of bearing the flowers usually on very long, single stems;

(3) Exceptionally long and very attractive urn-shaped buds;

(4) A moderately double flower form;

(5) An attractive, medium pink flower color; and (6) A strong flower fragrance.

In comparison with its seed parent, "First Love," the plant of the new variety is considerably more vigorous, the flower stems are very long in contrast to the more medium-length stems of this parent variety, and the flowers have a very strong fragrance in contrast to the little or no fragrance of the flowers of this parent.

As compared with the unnamed pollen parent, the plant of the new variety has considerably longer flower stems, the buds are long and an attractive urn-shape in form in contrast to the relatively short and fat buds of this parent, and the flower color of the new variety is pink in contrast to the light yellow flower color of this parent.

Asexual reproduction of our new variety by budding, as performed at Ontario, California, shows that the foregoing characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated as "Wilson") and Robert Ridgway's Color Standards and Nomenclature (hereinafter abbreviated as "Ridgway"), as indicated:

Type: Tall; bush; outdoor; seedling; for cut flowers and for garden decoration.

Class: Hybrid tea.

Breeding: Seedling.

*Seed parent.*—"First Love."

*Pollen parent.*—An unnamed seedling.

Propagation: Holds its distinguishing characteristics through succeeding propagations by budding.

*Flower*

Locality where grown and observed: Ontario, California.

Flowers borne: Usually singly, but sometimes several to stem; on strong, very long stems.

Quantity of bloom: Free outdoors.

Continuity: Nearly continuous during growing season.

Fragrance: Strong.

Bud:

*Peduncle.*—From average length to long; average caliper; erect; stiff; usually smooth; with from none to few small stipitate glands. Color—between Buffy Olive, Plate XXX (Ridgway) and Deep Chrysolite Green, Plate XXXI (Ridgway).

*Before calyx breaks.*—Size—from medium to large. Form—from medium length to long; ovoid.

*As calyx breaks.*—Color—between Cardinal Red, Plate 822, page 168 (Wilson) and Chrysanthemum Crimson, Plate 824/2, page 169 (Wilson).

*Sepals.*—Inner surface—lined with fine, wooly tomentum. Outer surface—smooth. Alternate margins—lined with fine wooly tomentum. Other margins—lined with few stipitate glands and few small, slender foliaceous appendages.

*As first petal opens.*—Size—average. Form—urn-shaped. Color: outside—between Tyrian Rose, Plate 24/2, page 24 (Wilson) and Rose Bengal, Plate 25/2, page 25 (Wilson), with small area at base of petal near Sulphur Yellow, Plate 1, page 1 (Wilson); inside—between Rose Bengal, Plate 25/2, page 25 (Wilson) and Rose Bengal, Plate 25/3, page 25 (Wilson), with small area at base of petal near Aureolin, Plate 3, page 3 (Wilson).

*Opening.*—Usually opens well, though there is a tendency for the flowers to be more cupped under some weather conditions.

Bloom:

*Size (when fully open).*—From average to large; from 3½ inches to 5 inches.

*Petalage.*—Double; from 30 to 40 petals, plus from none to few petaloids; arranged irregularly.

*Form.*—High centered at first, but becoming from cupped to high centered; petals being at first somewhat tightly cupped with tips reflexed outward, but later becoming from loosely flat to cupped, with tips reflexed outward at maturity.

Petals:

*Texture.*—Medium thickness.

*Appearance.*—Inside—satiny. Outside—satiny.

*Shape.*—Outside—between round and broadly obovate, with apex from rounded to flat, and usually with from one to three notches. Intermediate—broadly obovate, with apex rounded, and usually with one or two notches. Inside—between oval and obovate, with apex rounded, and usually with one or two notches.

This description of a newly opened flower was made from a rose grown outdoors during the month of September at Ontario, California:

*Color.*—Outer petal: outside surface—between Rose Bengal, Plate 25/2, page 25 (Wilson) and Solferino Purple, Plate 26/3, page 26 (Wilson), with small area at base of petal near Sulphur Yellow, Plate 1/1, page 1 (Wilson); inside surface—between Solferino Purple, Plate 26/3, page 26 (Wilson) and Magenta, Plate 27/3, page 27 (Wilson), with small area at base of petal near Aureolin, Plate 3, page 3 (Wilson). Intermediate petal: outside surface—between Tyrian Rose, Plate 24/2, page 24 (Wilson) and Rose Bengal, Plate 25/3, page 25 (Wilson), with small area at base of petal near Sulphur Yellow, Plate 1, page 1 (Wilson); inside surface—between Rose Bengal, Plate 25/2, page 25 (Wilson) and Solferino Purple, Plate 26/3, page 26 (Wilson), with small area at base of petal near Aureolin, Plate 3, page 3 (Wilson). Inner petal: outside surface—between Tyrian Rose, Plate 24/2, page 24 (Wilson) and Rose Bengal, Plate 25/3, page 25 (Wilson), with small area at base of petal near Sulphur Yellow, Plate 1, page 1 (Wilson); inside surface—between Rose Bengal, Plate 25/2, page 25 (Wilson) and Rose Bengal, Plate 25/3, page 25 (Wilson) with small area at base of petal near Aureolin, Plate 3, page 3 (Wilson).

This description was made from a rose that was open for three days outdoors during the month of September at Ontario, California:

*Color.*—Outer petal: outside surface—between Phlox Pink, Plate 625/3, page 77 (Wilson) and Fuchsine Pink, Plate 627/2, page 78 (Wilson), with small area at base of petal near Canary Yellow, Plate 2/2, page 2 (Wilson); inside surface—near Fuchsine Pink, Plate 627/3, page 78 (Wilson), with small area at base of petal near Aureolin, Plate 3/2, page 3 (Wilson). Inner petal: outside surface—between Rose Bengal, Plate 23/2, page 23 (Wilson) and Solferino Purple, Plate 26/3, page 26 (Wilson), with small area at base of petal near Carnary Yellow, Plate 2/1, page 2 (Wilson); inside surface—near Phlox Pink, Plate 625/2, page 77 (Wilson), with small area at base of petal near Aureolin, Plate 3/1, page 3 (Wilson).

*General color effect.*—Newly opened flower—between Tyrian Rose, Plate 24/2, page 24 (Wilson) Rose Bengal, Plate 25/3, page 25 (Wilson). 3-days open—between Phlox Pink, Plate 625/2, page 77 (Wilson) and Fuchsine Pink, Plate 627/3, page 78 (Wilson).

*Behavior.*—Drop off cleanly; not particularly affected by cold, hot, wet or dry weather.

*Flower longevity.*—On bush in garden—4 or 5 days in August. Cut roses grown outdoors and kept at living-room temperatures—from 3 to 6 days in August.

*Reproductive Organs*

Stamens: Average number; arranged regularly about pistils.

Filaments: From medium length to long (from 8 to 15 mm. long); most with anthers. Color—near Apricot, Plate 609/2 page 70 (Wilson).

Anthers: From small to medium size; all open approximately at once. Color: upper side—margins near Cadmium Orange, Plate 8/2, page 8 (Wilson), with remainder near Straw Yellow, Plate 604/2, page 67 (Wilson); under side—margins near Cadmium Orange, Plate 8/2, page 8 (Wilson), with remainder near Straw Yellow, Plate 604/2, page 67 (Wilson).

Pollen: Moderate abundance. Color—near Saffron Yellow, Plate 7, page 7 (Wilson).

Pistils: Many (from approximately 80 to 100 in number).

Styles: Moderately even; from short to average length; thin caliper, bunched. Color—near Uranium Green, Plate 63/2, page 63 (Wilson), with upper third of style overlaid with near Geranium Lake, Plate 20/1, page 20 (Wilson).

Stigma: Color—near Chrome Yellow, Plate 605/2, page 144 (Wilson).

Ovaries: Usually all enclosed in receptacle.

Hips: Average length; globular; smooth; walls thick and fleshy. Color (immature)—near Biscay Green, Plate XVII (Ridgway).

Sepals: Falling soon. Color: inside—near Mytho Green, Plate XLI (Ridgway); outside—near Apple Green, Plate XVII (Ridgway).

Seeds: From few to average number (from 6 to 15); from small to medium size.

*Plant*

Foliage:

*Leaves.*—Compound of usually 3–7 leaflets; from normal quantity to abundant; medium size; somewhat leathery; semi-glossy.

*Leaflets.*—Shape—between oval and ovate, with apex between acute and acuminate. Base—between round and acute. Margin—simply serrate.

*Color.*—Mature: upper surface—near Cress Green, Plate XXXI (Ridgway); under surface—near Light Grape Green, Plate XXXI (Ridgway). Young: upper surface—near Light Cress Green, Plate XXXI (Ridgway), overlaid with near Ocher Red, Plate XXVII (Ridgway) around edges; under surface—near Asphodel Green, Plate XLI (Ridgway), overlaid with near Corinthian Red, Plate XXVII (Ridgway).

*Rachis (the supporting stem of the compound leaf).*—Average size. Upper side—smooth; with from few to several stipitate glands on edges. Under side—smooth; with from none to few stipitate glands and from none to few small prickles.

*Stipules.*—Short; medium width; with short points turning out at an angle of less than 45°; usually recurved toward the stem.

*Disease resistance.*—Average resistance to mildew, as compared with other varieties grown under comparable cultural conditions at Ontario, California.

Growth:

*Habit.*—Upright; moderately branched.

*Growth.*—Very vigorous.

*Canes.*—From medium caliper to heavy.

*Main stems.*—Color—between Rainette Green, Plate XXXI (Ridgway) and Deep Grape Green, Plate XLI (Ridgway). Large prickles—from few to several; from short to medium length; hooked slightly downward; with medium length and moderately narrow base; color—near Cinnamon, Plate XXIX (Ridgway). Small prickles—from few to several; color—near Cinnamon, Plate XXIX (Ridgway). Hairs—none.

*Branches.*—Color—near Biscay Green, Plate XVII (Ridgway). Large prickles—from few to several; from short to medium length; hooked slightly downward; with medium length, narrow base; color—near Cinnamon Brown, Plate XV (Ridgway). Small prickles—very few; color—near Cinnamon Brown, Plate XV (Ridgway). Hairs—none.

*New shoots.*—Color—near Absinthe Green, Plate XXXI (Ridgway), with side exposed to sun overlaid with near Pecan Brown, Plate XXVIII (Ridgway). Large prickles—very few; short; almost straight; with short, narrow base; color—near Walnut Brown, Plate XXVIII (Ridgway). Small prickles—from none to few; color—near Walnut Brown, Plate XXVIII (Ridgway). Hairs—none.

We claim:

A new and distinct variety of rose plant of the hybrid tea class, substantially as herein shown and described, characterized particularly as to novelty by the unique combination of upright and exceptionally vigorous habits of growth, a habit of bearing the flowers usually on very long, single stems, exceptionally long and very attractive urn-shaped flower buds, moderately double open flowers, a distinctive and attractive medium pink general color tonality of the flowers, and a strong flower fragrance.

No references cited.